US006650938B2

(12) United States Patent
Boute (10) Patent No.: US 6,650,938 B2
(45) Date of Patent: Nov. 18, 2003

(54) METHOD AND SYSTEM FOR PREVENTING ATRIAL FIBRILLATION BY RAPID PACING INTERVENTION (75) Inventor: Willem Boute, Dieren (NL)

(73) Assignee: Medtronic, Inc., Minneapolis, MN (US)

(*) Notice: Subject to any disclaimer, the term of this patent is extended or adjusted under 35 U.S.C. 154(b) by 106 days.

(21) Appl. No.: 09/842,878

(22) Filed: Apr. 27, 2001

(65) Prior Publication Data
US 2003/0009198 A1 Jan. 9, 2003

(51) Int. Cl.$^7$ ................................. A61N 1/365
(52) U.S. Cl. ................. 607/14; 607/9; 607/25; 607/27
(58) Field of Search ................ 607/9, 14, 25, 607/2, 30, 17, 40, 27, 6

(56) References Cited

U.S. PATENT DOCUMENTS

| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson et al. |
| 4,549,719 A | 10/1985 | Baumann |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann |
| 4,727,877 A | 3/1988 | Kallok |
| 4,821,723 A | 4/1989 | Baker et al. |
| 4,830,006 A | 5/1989 | Haluska et al. |
| 4,880,005 A | 11/1989 | Pless |
| 4,953,551 A | 9/1990 | Mehra |
| 5,117,824 A | 6/1992 | Keimel |
| 5,131,388 A | 7/1992 | Pless |
| 5,144,949 A | 9/1992 | Olson |
| 5,158,078 A | 10/1992 | Bennett |
| 5,207,218 A | 5/1993 | Carpentier |
| 5,312,453 A | 5/1994 | Shelton et al. |
| 5,314,430 A | 5/1994 | Bordy |
| 5,330,507 A | 7/1994 | Schwartz |
| 5,331,966 A | 7/1994 | Bennett |
| 5,354,316 A | 10/1994 | Keimel |
| 5,545,186 A | 8/1996 | Olson |
| 5,713,929 A | 2/1998 | Hess et al. |
| 5,800,465 A | 9/1998 | Thompson et al. |

OTHER PUBLICATIONS

"A new pacing algorithm for overdrive suppression of atrial fibrillation" Murgatroyd et al. PACE, Nov. 1994, pp 1996–1973.
"Pacing straregies to prevent atrial fibrillation" Fahy et al. Cardiology Clinic Nov. 1996, pp 591–596.
"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.
"Automatic Tachycardia Recognition" Arzbaecher et al. PACE, May–Jun. 1984 p. 541–547.

Primary Examiner—Hieu T. Vo
Assistant Examiner—Johnny H. Hoang
(74) Attorney, Agent, or Firm—Thomas F. Woods; Eric R. Waldkoetter; Tom G. Berry (57) ABSTRACT A method of pacing cardiac tissue using an implantable medical device is provided. A first fibrillation-indicative interval is determined based on a first fibrillation-indicative event. A first adjusted pacing interval, wherein the first adjusted pacing interval is shorter than the first fibrillation-indicative interval, is determined and the cardiac tissue is paced based on the first adjusted pacing interval. If the cardiac tissue is not captured by pacing at the first adjusted pacing interval, an additional fibrillation-indicative interval is determined based on an additional earlier fibrillation-indicative event. An additional adjusted pacing interval, wherein the additional adjusted pacing interval is shorter than the additional fibrillation-indicative interval is determined and the cardiac tissue is paced based on the additional adjusted pacing interval.

53 Claims, 7 Drawing Sheets

METHOD AND SYSTEM FOR PREVENTING ATRIAL FIBRILLATION BY RAPID PACING INTERVENTION

FIELD OF THE INVENTION

The present invention relates to the field of implantable medical devices. More particularly, the present invention relates to cardiac pacing systems that provide a method for preventing atrial fibrillation by rapid pacing intervention.

BACKGROUND OF THE INVENTION

Tachyarrhythmias are episodes of high-rate cardiac depolarizations. Tachyarrhythmias may occur in one chamber of the heart or may be propagated from one chamber to another. Some tachyarrhythmias are sufficiently high in rate to compromise cardiac output from the chamber(s) affected, leading to loss consciousness or death, in the case of ventricular fibrillation or weakness and dizziness in the case of atrial fibrillation. Atrial fibrillation is often debilitating, due to the loss of atrial cardiac output, and may sometimes lead to ventricular fibrillation.

Generally, fibrillation may be terminated by administering high energy level cardioversion/defibrillation shocks or pulses until the fibrillation is terminated. For example, in the context of implantable anti-arrhythmia devices, these pulses may be applied by means of large surface area electrodes on or in the chamber to be defibrillated. However, the high energy level pulses are often sufficient to cause pain to the patient. Moreover, in some cases an atrial defibrillation pulse is delivered at an inappropriate time and may cause ventricular arrhythmias. Thus, it would be desirable to prevent or decrease the occurrence of atrial fibrillation.

Implantable pulse generators (IPGs) that deliver pacing level pulses are well known in the art. In some cases, patients already having an IPG are the same patients susceptible to atrial fibrillation. It would thus also be desirable to administer preventive measures against atrial fibrillation using the IPGs already implanted in the patient.

Some IPGs are equipped to sense Premature Atrial Contractions (PACs) and/or Premature Ventricular Contractions (PVCs). PACs/PVCs may be used to indicate the onset of a cardiac event such as an atrial fibrillation. It would also be desirable, therefore, to use PACs, PVCs and other "trigger" events that indicate the onset of atrial fibrillation to help prevent or decrease the occurrence of atrial fibrillation.

Thus, a need exists in the medical arts for using cardiac "trigger" events that indicate the onset of atrial fibrillation and rapid pacing intervention to prevent or decrease the occurrence of atrial fibrillation.

Some methods have been proposed in the prior art for the prevention of atrial fibrillation using pacing pulses.

For example, U.S. Pat. No. 5,713,929 to Hess et al. discloses a pacing algorithm which paces the heart at a faster than indicated rate during detection of PACs/PVCs. The algorithm then reduces the pacing rate to a safety rate unless natural depolarizations are detected.

The article "A New Pacing Algorithm for Overdrive Suppression of Atrial Fibrillation" by Murgatroyd, et al. in the journal PACE discloses increasing the atrial rate by 12.5% following detection of a PAC. The rate is then decreased by 63 msec until the lower rate is reached or intrinsics are sensed.

The article "Pacing Strategies to Prevent Atrial Fibrillation" by Fahy, et al. in the journal Cardiology Clinics discloses overdrive pacing to prevent fibrillation.

The publication from Quintech regarding "Quintech Dynamic Overdrive" discloses atrioventricular sequential pacing at the upper rate limit after atrial fibrillation has ended.

The most pertinent prior art publications known at the present time are shown in the following table:

TABLE 1

| Prior Art Publications | | |
|---|---|---|
| Patent No. | Date | Inventor(s) |
| 5,713,929 | Feb. 3, 1998 | Hess et al. |

Murgatroyd, et al. (November 1994) "A New Pacing Algorithm for Overdrive Suppression of Atrial Fibrillation". *PACE,* Volume 17, Part II, pp. 1966–1973.

Fahy, et al. (November 1996) "Pacing Strategies to Prevent Atrial Fibrillation". *Cardiology Clinics.* Volume 14, Number 4, pp. 591–596. "Quintech Dynamic Overdrive"

The publications listed in Table 1 are hereby incorporated by reference herein, each in its entirety. As those of ordinary skill in the art will appreciate readily upon reading the Summary of the Invention, the Detailed Description of the Preferred Embodiments and the Claims set forth below, at least some of the devices and methods disclosed in the patent of Table 1 may be modified advantageously in accordance with the teachings of the present invention.

SUMMARY OF THE INVENTION

The present invention is therefore directed to providing a method and system for preventing atrial fibrillation by pacing at a slightly shorter interval than the PAC coupling interval once a first PAC has been sensed and pacing at an even more aggressive interval once an additional PAC is sensed. The system of the present invention overcomes at least some of the problems, disadvantages and limitations of the prior art described above, and provides a more efficient and accurate means of preventing atrial fibrillation.

The present invention has certain objects. That is, various embodiments of the present invention provide solutions to one or more problems existing in the prior art respecting the pacing of cardiac tissue. Those problems include, without limitation: (a) patients experiencing discomfort from atrial fibrillation; (b) difficulty in administering high energy stimulus pulses to treat atrial fibrillation, (c), difficulty in administering therapy for atrial fibrillation using pacing pulses; (d) difficulty in providing pacing pulses at appropriate intervals to prevent atrial fibrillation; and (e) difficulty in using PACs, PVCs and other cardiac "trigger" events to signal onset of atrial fibrillation.

In comparison to known pacing techniques, various embodiments of the present invention provide one or more of the following advantages: (a) the use of pacing energy level pulses to prevent or decrease the occurrence of atrial fibrillation; (b) the ability to detect the onset of possible atrial fibrillation (c) the ability to adjust pacing intervals for use in prevention of atrial fibrillation, (d) the ability to decrease or prevent the occurrence of atrial fibrillation, (e) the ability to use already-implanted IPGs to administer therapy for atrial fibrillation and (f) fewer patient complaints of discomfort in the treatment of fibrillation.

Some embodiments of the present invention include one or more of the following features: (a) an IPG capable of preventing atrial fibrillation; (b) an IPG capable of sensing potential atrial fibrillation and adjusting pacing intervals to prevent the fibrillation from occurring; (c) methods of preventing atrial fibrillation with pacing energy level pulses rather than high energy shocks and (d) methods of sensing potential atrial fibrillation and adjusting pacing intervals to prevent the fibrillation from occurring.

At least some embodiments of the present invention involve pacing cardiac tissue based on an initial pacing interval. A first fibrillation-indicating event is detected. A first adjusted pacing interval is determined. The cardiac tissue is paced based on the first adjusted pacing interval for a first duration in an attempt to capture the cardiac tissue. If the first adjusted pacing interval does not capture the cardiac tissue, an additional fibrillation-indicating event may have occurred earlier to the first fibrillation-indicating event and may be detected. An additional adjusted pacing interval may then be determined and the tissue paced according to the additional adjusted pacing interval in a further attempt to capture the cardiac tissue.

BRIEF DESCRIPTION OF THE DRAWINGS

The above, and other objects, advantages and features of the present invention will be more readily understood from the following detailed description of the preferred embodiments when considered in conjunction with the drawings, in which like reference numerals indicate identical structures throughout the several views, and wherein.

DETAILED DESCRIPTION OF THE PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
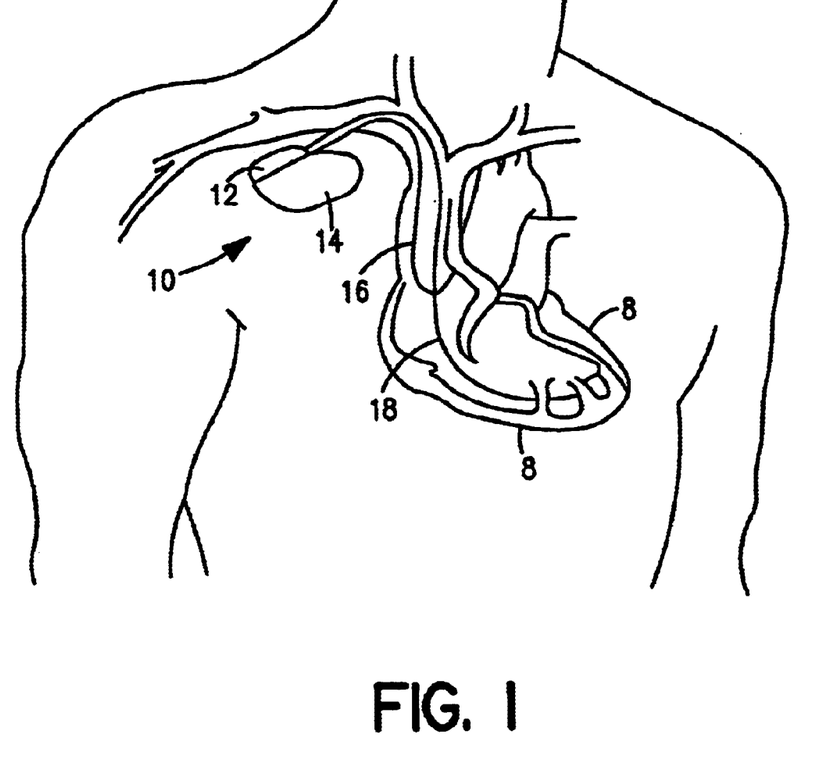
FIG. 1 is a schematic view of one embodiment of an implantable medical device in situ, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. One or more of leads 16 and 18 may be used to sense PACs or PVCs in accordance with the present invention. One or more of leads 16 and 18 may also serve to administer pacing pulses for the prevention of atrial fibrillation in accordance with the present invention. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference herein, each in its respective entirety.

Figure 2:
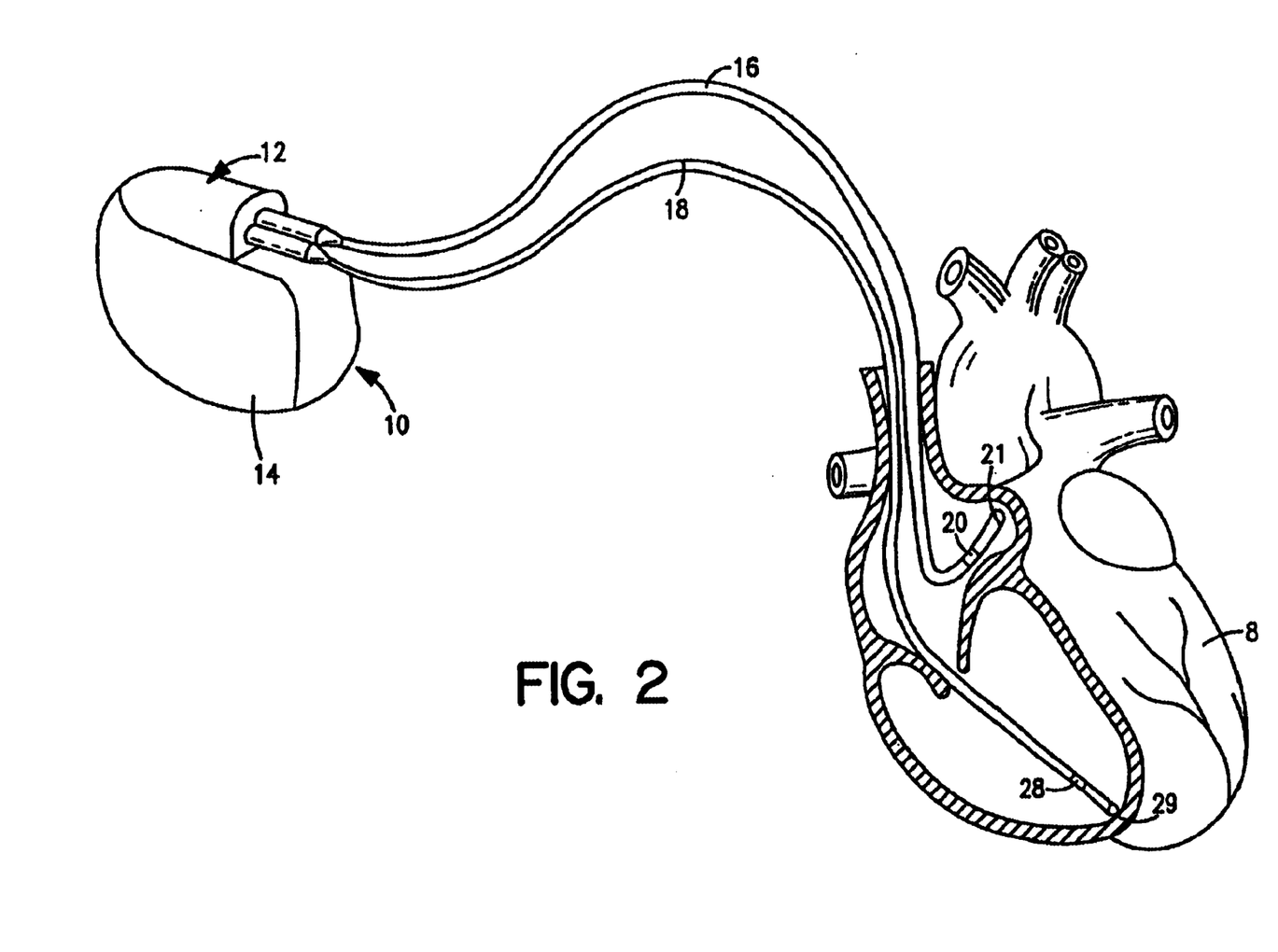
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
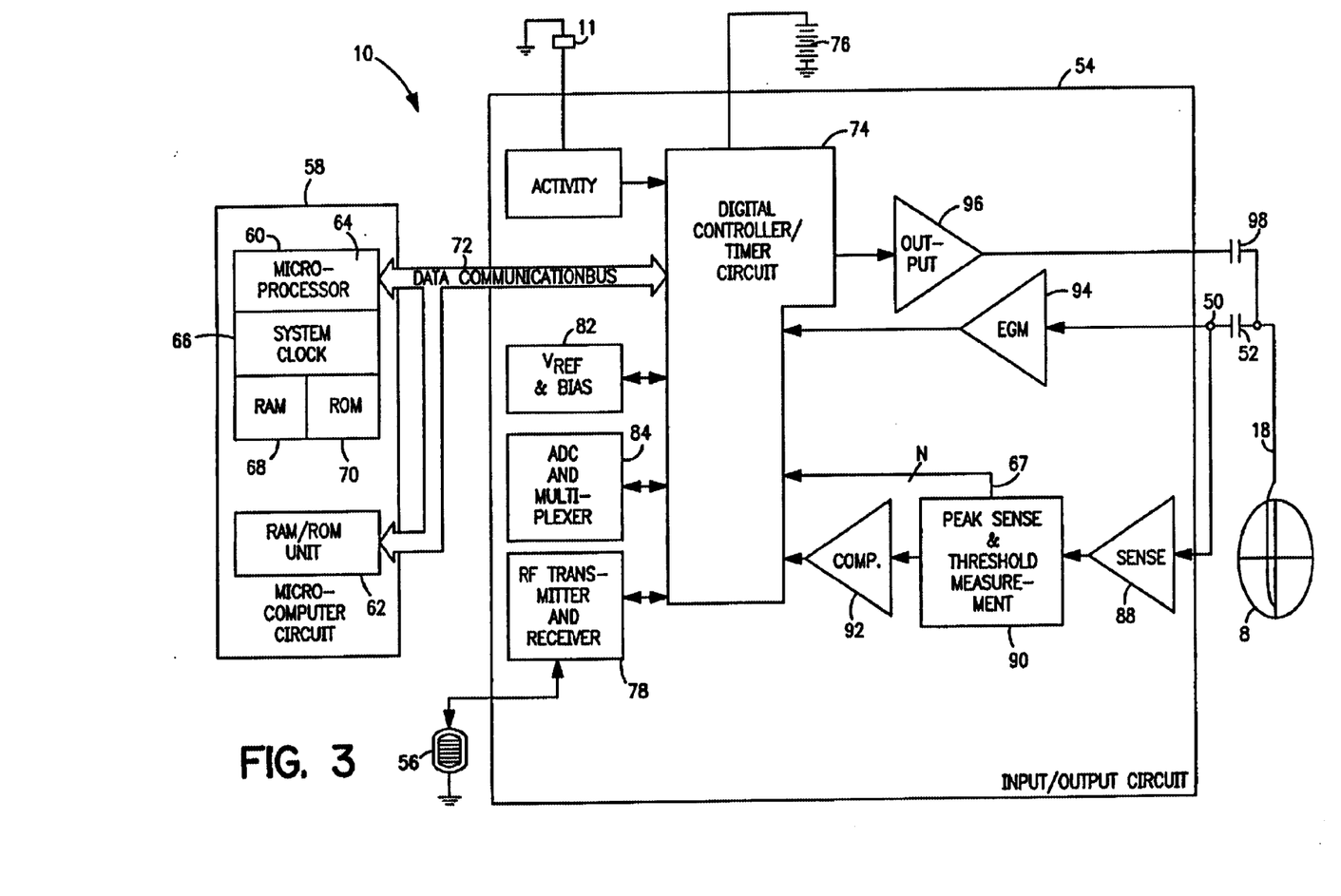
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which may be an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16. In one embodiment of the invention, activity sensor 11 may be used to detect PACs and/or PVCs.

IMD 10 in FIG. 3 may be programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in U.S. Pat. No. 5,312,453 to Wyborny et al. is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 may be attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. Accordingly, the rate at which heart 8 is stimulated or beats spontaneously without stimulation may be controlled and/or monitored using software-implemented algorithms or pacing rate functions stored in microcomputer circuit 58. One such algorithm may be used to pace cardiac tissue at an interval slightly shorter than a PAC coupling interval in response to the sensing of a first PAC. The cardiac tissue may be paced at a constant rate followed by a slow decrease unless an additional PAC is sensed. If an additional PAC is sensed, the pacing interval may be further shortened.

Microcomputer circuit 58 may comprise on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 may include microprocessor 64, system clock circuit 66 and on-board RAM 68 and ROM 70. Off-board circuit 62 may comprise a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 may generate stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 may be coupled to sensing circuitry, including sense amplifier 88, peak sense and threshold measurement unit 90 and comparator/threshold detector 92. Circuit 74 may further be coupled to electrogram (EGM) amplifier 94 for receiving amplified and processed signals sensed by lead 18, such as PACs or PVCs indicating potential atrial fibrillation. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, each time an externally transmitted pacing command is received or in response to other stored commands as is well known in the pacing art. In one embodiment of the invention, the escape interval is set to an interval slightly shorter than the PAC coupling interval once a first PAC has been sensed. Upon sensing of an additional PAC, the atrial escape interval is set at an even more aggressive interval. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, WI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated, such as, for example, PACs indicating potential atrial fibrillation. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference herein, each in its respective entirety.

Figure 4:
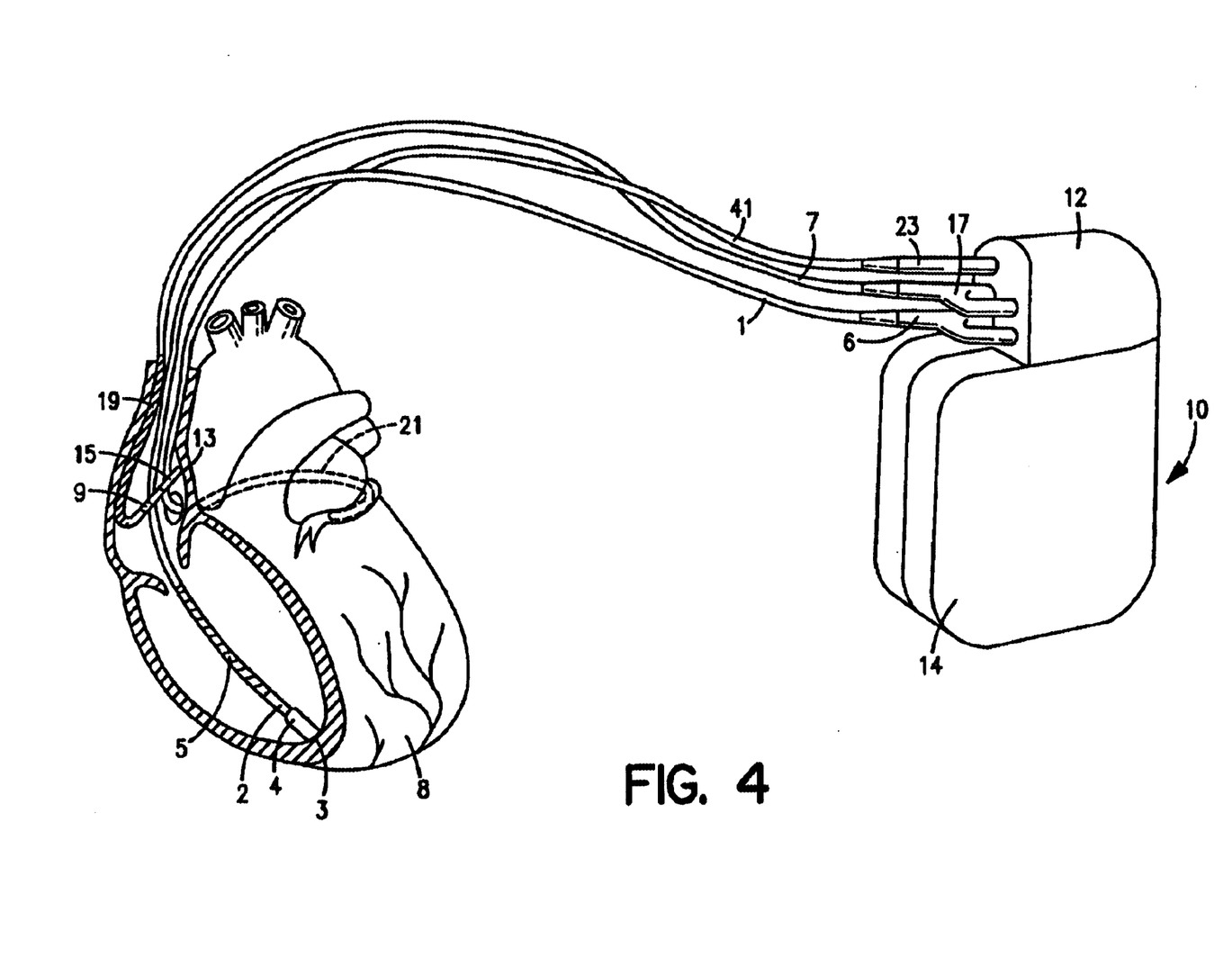
FIG. 4 is a schematic view of another embodiment of an implantable medical device, made in accordance with the present invention.
Figure 5:
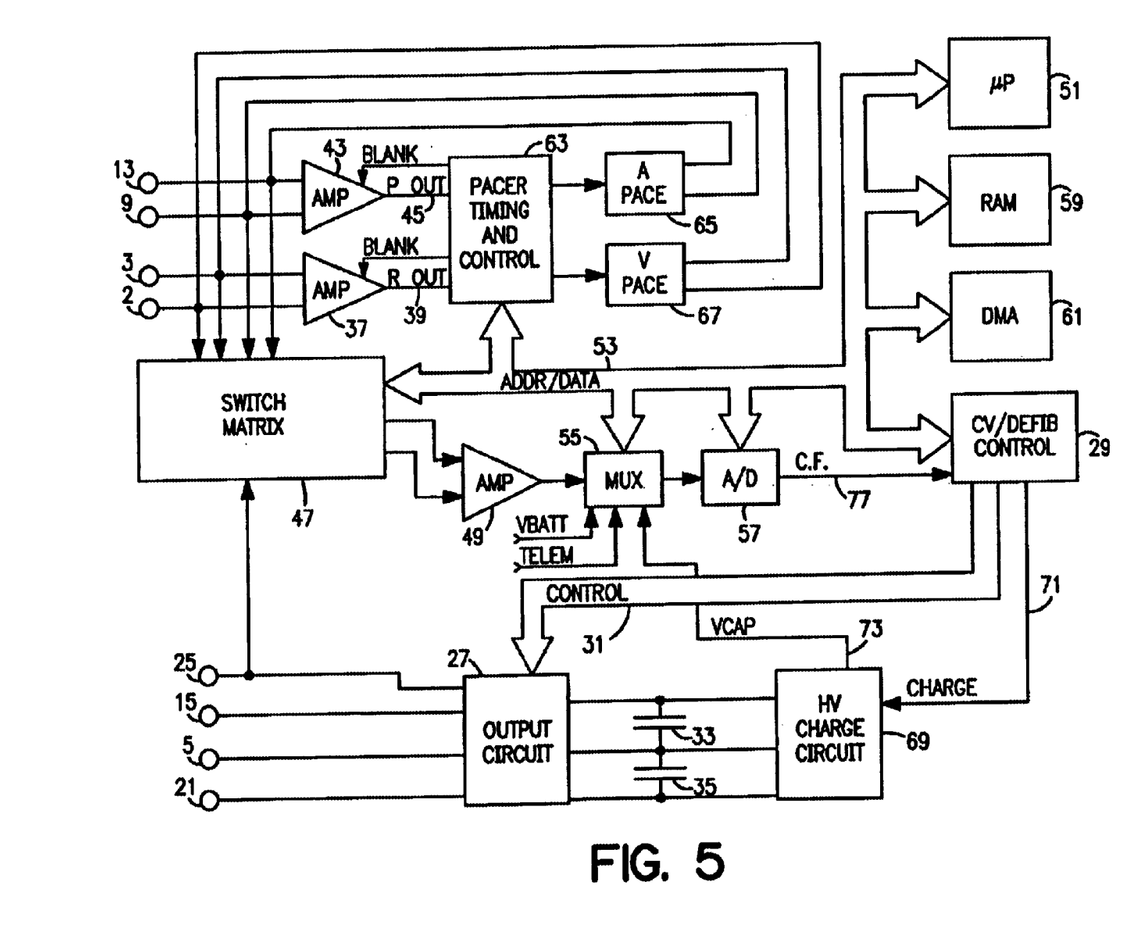
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 may be employed for cardiac pacing and for sensing ventricular depolarizations.

At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 may be employed for atrial pacing and for sensing atrial depolarizations. Elongated coil electrode 19 is provided proximal to electrode 9 and coupled to the third conductor within lead body 7. In one embodiment of the invention, electrode 19 is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which may take the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which may also take the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. A signal may also be generated indicating a PAC. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 may include programmable digital counters which control the basic time intervals associated with DDD, WI, DVI, VDD, AAI, DDI and other modes of single and dual chamber pacing well known to the art. Circuitry 63 also may control escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. In one embodiment of the invention, escape interval counters may also be reset to generate pacing pulses at intervals aggressive enough to prevent atrial fibrillation. The durations of the intervals defined by escape interval timers are determined by microprocessor 51 via data/address bus 53. The value of the count present in the escape interval counters when reset by sensed R-waves and P-waves may be used to measure the durations of R—R intervals, P-P intervals, P-R intervals and R-P intervals, which measurements are stored in memory 59 and used to detect the presence of tachyarrhythmias. The value of the count present in the counter when reset by sensing of a first PAC may also be used to calculate a slightly shorter pacing interval for additional pacing in order to prevent atrial fibrillation.

Microprocessor 51 may operate as an interrupt driven device, and may be responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts. For example, a more aggressive, i.e., slightly shorter, pacing interval may be calculated.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference herein, each in its respective entirety.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters. For example, the escape interval counters may be set in accordance with the present invention at a more aggressive, i.e., slightly shorter interval, to prevent atrial fibrillation.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated herein by reference, each in its respective entirety, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat.

No. 4,375,817 to Engle et al., all of which are hereby incorporated by reference herein, each in its respective entirety, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference herein in its entirety.

An example of circuitry that may be used to control delivery of monophasic pulses is disclosed in U.S. Pat. No. 5,163,427 to Keimel, also hereby incorporated by reference herein in its entirety. Output control circuitry similar to that disclosed in U.S. Pat. No. 4,953,551 to Mehra et al. or U.S. Pat. No. 4,800,883 to Winstrom, both incorporated by reference, each in its respective entirety, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
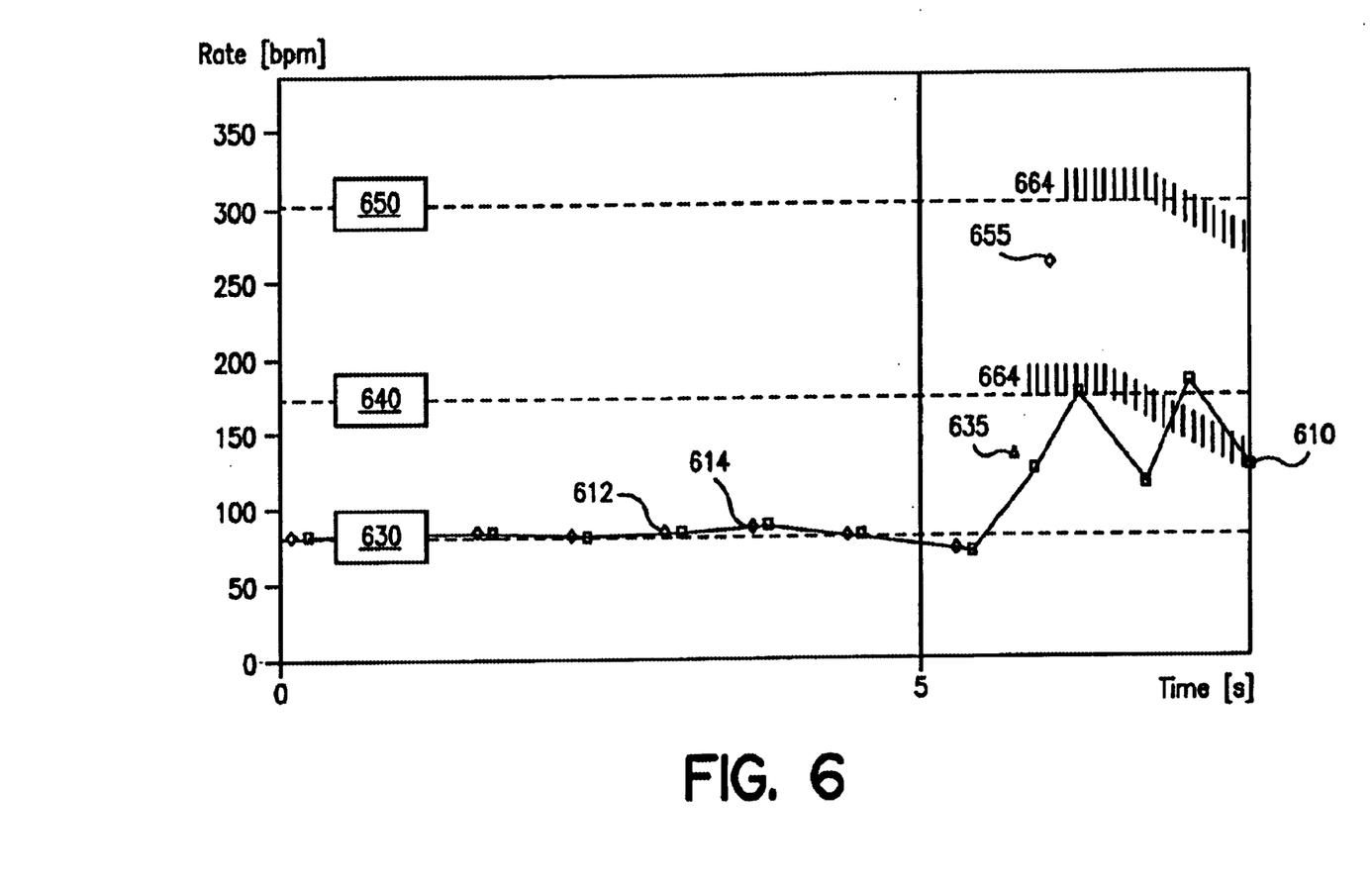
FIG. 6 is a graph illustrating one embodiment of a pacing interval being modified to prevent atrial fibrillation in accordance with the present invention.

FIG. 6 shows a graph illustrating the operation of one embodiment of the present invention, where a pacing rate delivered by IMD 10 disposed within mammalian heart 8 is adjusted to a more aggressive pacing interval after a first PAC is sensed during time period 600. In one embodiment of the present invention, the shortened pacing interval is used to prevent fibrillation of heart 8.

Time period 600 is the period of time over which rapid pacing intervention occurs and the pacing interval changes in response to the potential fibrillation. Time period 600 shown in FIG. 6 is a 5.5 seconds, but also may range, without limitation, between about 0 to 10 seconds, 0.25 to 8 seconds, and 0.5 to 6 seconds although both higher and lower time period values are possible for time period 600.

In FIG. 6, a heart rate function of heart 8 may be represented by heart rate function 610. Heart rate function 610 may be representative of the atrial or the ventricular rate at which heart 8 beats when no electrical stimulation is provided thereto (i.e., the unpaced heart rate). Alternatively, heart rate function 610 may be representative of the atrial heart rate or the ventricular heart rate of a heart 8 influenced by pacing therapy which may include provisions for determining, setting and/or implementing a lower rate limit function (i.e., the lowest rate at which a patient's heart is permitted to be paced), an upper rate limit function (i.e., the highest rate at which a patient's heart is permitted to be paced), or both lower and upper rate limit functions (i.e., pacing rate function 610 may comprise both upper and lower rate limit functions). In the embodiment shown in FIG. 6, heart rate function 610 reflects a ventricular heart rate function.

The various rates at which heart rate function 610 occurs may be determined initially by the settings of the software-implemented algorithms associated therewith, may be determined on the basis of data gathered or acquired by IMD 10, may be preprogrammed, or may be set by the attending physician. By way of example, heart rate function 610 may change or be adjusted in linear, non-linear, step-wise, asymptotic, logarithmic, exponential and/or geometric fashion, or in any suitable combination or permutation of the foregoing.

It is important to note that FIG. 6 illustrates merely one embodiment of the present invention, and is not intended the limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

As seen in FIG. 6, initial pacing rate 630 of heart rate function 610 may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of pacing rates 630 that have been determined to be acceptable and that are stored in microcomputer 58. Similar procedures and means may be employed and implemented when determining initial values for a lower pacing rate limit and upper pacing rate limit. Values for initial pacing rate 630 may range, for example, between about 25 bpm and about 95 beats ppm, between about 30 bpm and about 80 bpm, between about 35 bpm and about 65 bpm, and between about 50 bpm and about 65 bpm. Alternatively, initial pacing rate 630 may be equivalent to the rate at which heart 8 beats when no electrical stimulation is provided thereto (i.e., the unpaced heart rate). In the embodiment shown in FIG. 6, the initial rate 630 is approximately 90 bpm although other values are possible.

In one embodiment of the invention, a cardiac event, such as a first PAC may be sensed, for example as indicated at point 635 of FIG. 6. For comparison, point 612 may represent a regular atrial contraction occurring in time to initial rate 630. Point 614 may represent the subsequent atrial contraction following point 612 and occurring in time to initial rate 630. For example, at 90 bpm, the interval between points 612 and 614 is about 670 ms. As seen at point 635, the atrial contraction occurring at point 635 is premature, occurring at an interval before expected. Put another way, the contraction represented by point 612 may occur at a rate of approximately 90 bpm while the contraction represented by point 635, if allowed to continue, would be occurring at a rate of 140 bpm. In other words, the interval would decrease to about 420 ms if the precedent set by the PAC at point 635 were allowed to continue.

Preliminary analysis of atrial fibrillation onset mechanisms has revealed that several different cardiac events exist which indicate, or in some cases may initiate, atrial fibrillation. One such event is the PAC indicated by point 635.

These cardiac events may occur just prior to the onset of atrial fibrillation. These cardiac events may occur for example, five to ten seconds before atrial fibrillation starts. These cardiac events may include, without limitation, sudden onset of atrial fibrillation, short-long beats, short-long beats occurring post-PAC, multiple preceding PACs, or a sudden drop in heart rate. Once the first PAC, or other AF-indicative cardiac event is sensed, pacing function 610 may be set to intervene at the very onset of atrial fibrillation in an attempt to capture the atrium while it may still be captured, i.e., before atrial fibrillation renders the atrium difficult to capture.

In one embodiment of the invention, heart rate function 610 is paced in such a manner that pacing occurs at a more aggressive interval. For example, pacing pulses may be administered at a slightly shortened interval in comparison to the interval of initial pacing rate 630. This shortened interval may result in a first adjusted pacing rate 640 which may be later decayed to return to or near initial rate 630. One example of such pacing at rate 640 followed by a decay is indicated by bars 640 in FIG. 6. Additionally, pacing pulses may be administered at an interval shorter than the trigger event coupling interval. For example, as indicated by the bars at 644, the atrium of heart 8 may be paced at a more aggressive rate of 170 bpm or an interval of 350 ms in an attempt to capture the atrium. This pacing interval is shorter than the interval of the PAC (which is about 400 ms) but is a longer interval than that of a sustained atrial fibrillation. This pacing interval may be maintained for a duration before being decayed as shown by the bars at 644. In the embodiment of FIG. 6, this rate 640 decays to approximately 120 bpm over time. In one embodiment, the rate is decayed or decreased slowly, e.g., the interval is increased slowly, for example, from 0.1 to 4 ppm/beat. The duration for which heart 8 may be paced aggressively may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of duration that have been determined to be acceptable and that are stored in microcomputer 58.

In the embodiment shown in FIG. 6, an additional PAC may be sensed, for example, as indicated at point 655. In one embodiment of the invention, the additional PAC may occur even more prematurely than the first sensed PAC. For example, the additional PAC may occur at an interval ranging from 220–260 ms. In the embodiment shown in FIG. 6, for example, the atrial contraction represented at point 655, if allowed to continue, would be occurring at a rate of 270 bpm. In other words, the interval would decrease to about 220 ms if the precedent set by the PAC at point 655 were allowed to continue.

In such cases, pacing function 610 may be set to occur at an even more aggressive interval. For example, pacing pulses may be administered at an even shorter interval than the interval of adjusted pacing rate 640, resulting in an additional adjusted pacing rate 650. Adjusted pacing rate 650 could be, for example, as short as 150–250 ms. For example, as indicated by the bars at 664 in FIG. 6, the atrium of heart 8 may be paced at a more aggressive rate of 300 bpm or an interval of 200 ms in an attempt to capture the atrium. This pacing interval is shorter than the interval of the additional PAC (which is about 220 ms) but is a longer interval than that of a sustained atrial fibrillation. This pacing interval may be maintained for a duration before being decayed as shown by the bars at 664. In the embodiment of FIG. 6, this rate 650 decays to approximately 250 bpm over time. In one embodiment, the rate is decayed or decreased slowly, e.g., the interval is increased slowly, for example, from 0.1 to 4 ppm/beat. The duration for which heart 8 may be paced aggressively may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of duration that have been determined to be acceptable and that are stored in microcomputer 58.

Figure 7:
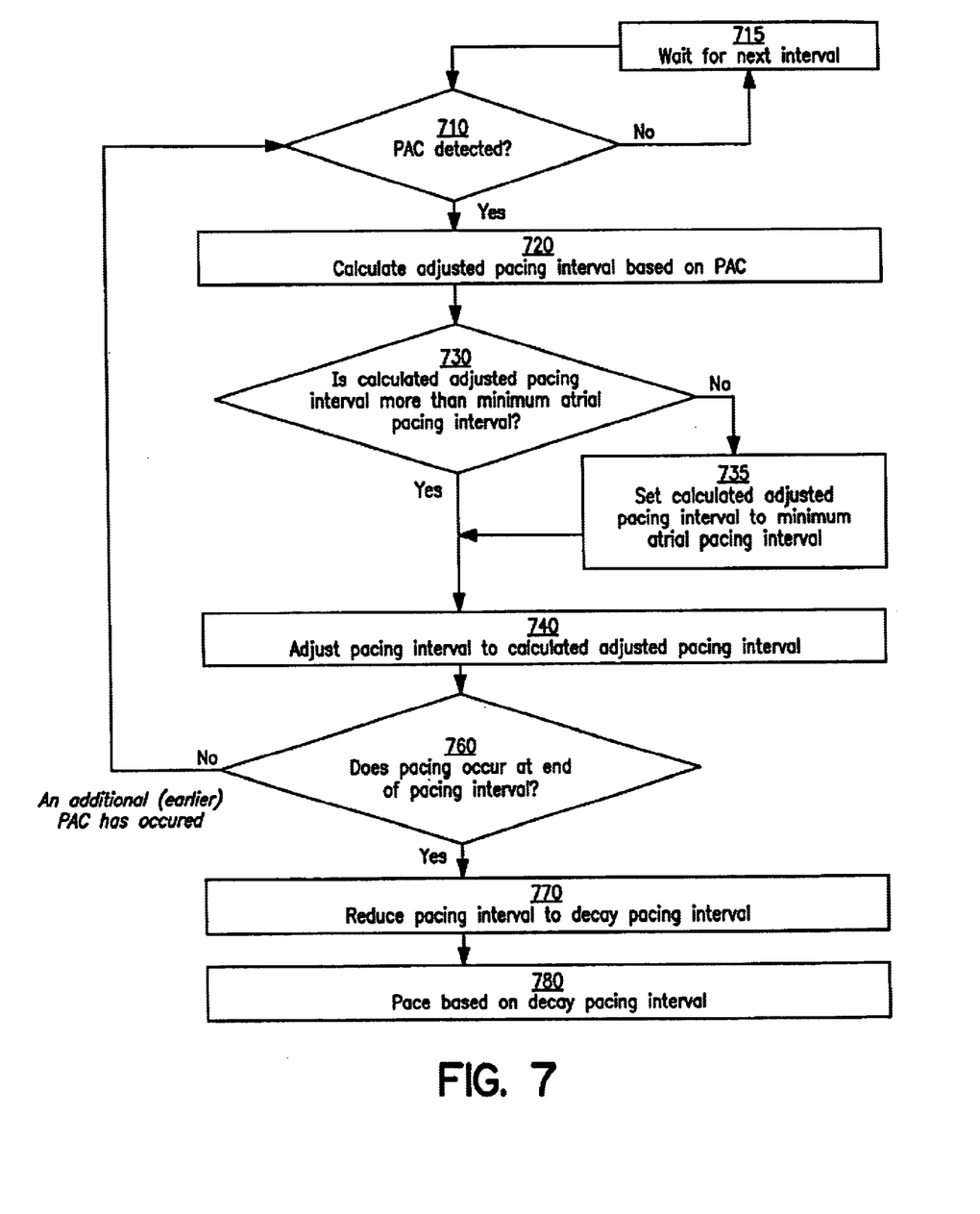
FIG. 7 is a flow diagram of one embodiment of a method for modifying a pacing interval to prevent atrial fibrillation in accordance with the present invention.

FIG. 7 illustrates one embodiment of a method for preventing atrial fibrillation by rapid pacing intervention in accordance with the teachings of the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

Before the routine begins, heart 8 may be paced or may be beating with no electronic stimulation (i.e., unpaced) at an initial heart rate. This initial rate 630 may be determined in accordance with one or more of the methods of determining same described above.

As seen at block 710, at any specific point during the beating of heart 8, it may be determined whether a PAC or other such fibrillation-indicative event is detected. In one embodiment of the invention, this determination is made periodically. For example an appropriate computer algorithm stored in memory or a portion of memory of microcomputer 58 of IMD 10 may constantly or periodically evaluate heart 8 for the occurrence of a PAC. Alternatively, the PAC may be sensed. The PAC may be sensed, for example, by one or more of the sensing leads described above or by activity sensor 11. If no PAC has been sense, the method may return to block 715 and wait for the next interval before a new detection of PACs is conducted. Meanwhile, at block 715, heart 8 may continue to beat at an initial unpaced or initial paced rate.

At block 720, if a PAC has been sensed, an adjusted pacing interval is calculated. For example, the adjusted pacing interval may be calculated based on the interval of the PAC, on the coupling interval of the PAC or on the number of sequential PACs detected. In one embodiment of the invention, the interval of the PAC is determined and the adjusted pacing interval is calculated as an interval shorter than the interval of the PAC. For example, the adjusted pacing interval may be calculated according to either or both of Equations (a) or (b) below:

$$\frac{\text{Adjusted}}{\text{Pacing interval}} = \frac{\text{PAC coupling}}{\text{interval}} - \frac{\text{percentage of PAC}}{\text{coupling interval}} \quad \text{Equation (a)}$$

$$\frac{\text{Adjusted}}{\text{Pacing interval}} = \frac{\text{PAC coupling}}{\text{interval}} - x \text{ msecs} \quad \text{Equation (b)}$$

In the above equations, the percentage of PAC coupling interval or the variable x may be set by the attending physician, determined on the basis of diagnostic data gathered or sensed by IMD 10, external diagnostic means or a physician, and/or determined by comparison to a database or look-up table comprising singular values or ranges of values of suitable percentages or variables that have been determined to be acceptable and that are stored in microcomputer 58.

At block 730, it may be determined whether or not the calculated adjusted pacing interval is more than a minimum atrial pacing interval. The minimum atrial pacing interval may be set by the attending physician, determined on the basis of diagnostic data gathered or sensed by IMD 10, external diagnostic means or a physician, and/or determined by comparison to a database or look-up table comprising singular values or ranges of values of suitable minimum pacing intervals that have been determined to be acceptable and that are stored in microcomputer 58.

If the calculated adjusted pacing interval is less than the minimum pacing interval, the calculated adjusted pacing interval may be set to equal the minimum pacing interval as seen at block 735. In this manner, a limit may be provided to the atrial pacing interval and or to the calculated adjusted pacing interval.

If the calculated adjusted pacing interval is more than the minimum pacing interval, the method may proceed to block 740. At block 740, heart 8 may then be paced according to the new pacing rate resulting from the calculated adjusted pacing interval. In one embodiment of the invention, the heart is paced at a rate based on adjusted pacing interval 640. The heart may be paced at the adjusted pacing interval for a duration such as a preprogrammed duration, or a duration set by a physician, selected from a look-up table or database, or calculated. The duration may range anywhere between a few beats to several minutes.

Alternatively, the heart may be paced at the calculated adjusted pacing interval while an evaluation is made at block 760 as to whether pacing occurs at the end of the pacing interval. In other words, a determination may be made as to whether the atrium is captured and the heart is again being paced.

If it is determined that pacing does occur at block 760, the adjusted pacing interval may then be reduced as indicated at block 770. In one embodiment of the invention, the pacing rate is reduced gradually or decayed. For example, the pacing rate may be reduced by gradually lengthening the pacing interval. In one embodiment of the invention, the pacing rate is gradually decayed until it returns to the initial pacing rate 630. The speed at which the decay occurs may be programmable, may be set by the attending physician, determined on the basis of diagnostic data gathered or sensed by IMD 10, external diagnostic means or a physician, and/or determined by comparison to a database or look-up table comprising singular values or ranges of values of suitable decay intervals that have been determined to be acceptable and that are stored in microcomputer 58.

At block 780, the heart may then be paced at a reduced pacing rate. This pacing rate may be, for example, the initial pacing rate 630. Alternatively heart 8 may be paced at any pacing rate suitable for continuing satisfactory pacing therapy. For example, heart 8 may be paced at a rate higher than the initial pacing rate but less than the aggressive rates used to prevent AF above.

If it is determined that pacing does not occur at block 760, the method may return to block 710 where it is determined whether an additional PAC has been detected. As seen in FIG. 7, if pacing does not occur at block 760, this may be a de facto indication that an additional, even earlier, PAC has occurred. If an additional PAC has been detected, the method may calculate an additional, even more aggressive adjusted pacing interval based on the second PAC.

Sensing of additional PACs in additional to the first PAC may occur an unlimited number of times. Accordingly, adjustment of the pacing interval may also conceivably occur an unlimited number of times. In one embodiment of the invention, adjustment of the pacing interval continues, based on calculated adjusted pacing intervals that may grow continually more aggressive, until the atrium is captured at block 760 or pacing resumes at the end of the pacing interval at block 760.

In the embodiment of the invention seen in FIG. 7, the parameters determined include: initial pacing rate based on initial pacing interval, adjusted pacing interval, adjusted pacing rate based on adjusted pacing interval, additionally adjusted pacing interval, additionally adjusted pacing rate based on additionally adjusted pacing interval and durations for pacing at adjusted pacing rates. One or any suitable combination of these parameters may be varied in accordance with the present invention. Alternatively, one or more of these parameters may be set at a desired value while one or more other parameters are varied in accordance with the present invention. Moreover, although the parameters are shown as being determined in a given order, these parameters may be determined in any combination and in any order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the increase of pacing parameters, per se, but may find further application as a measuring means. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method of pacing cardiac tissue using an implantable medical device, comprising:

determining a first fibrillation-indicative interval based on a first fibrillation indicative event;

determining a first adjusted pacing interval, wherein the first adjusted pacing interval is shorter than the first fibrillation-indicative interval;

pacing the cardiac tissue based on the first adjusted pacing interval;

determining if the cardiac tissue is captured by pacing at the first adjusted pacing interval;

if the cardiac tissue is not captured, determining an additional fibrillation indicative interval based on an additional earlier fibrillation-indicative event;

determining an additional adjusted pacing interval, wherein the additional adjusted pacing interval is shorter than the additional fibrillation-indicative interval; and pacing the cardiac tissue based on the additional adjusted pacing interval to reduce atrial fibrillation.

2. The method of claim 1, further comprising:
pacing the cardiac tissue based on an initial pacing interval.

3. The method of claim 1 wherein the additional adjusted pacing interval is shorter than the first adjusted pacing interval.

4. The method of claim 1 further comprising: detecting the first fibrillation-indicative event.

5. The method of claim 1 further comprising: detecting the additional earlier fibrillation-indicative event.

6. The method of claim 1 wherein the fibrillation-indicative event is a premature atrial contraction.

7. The method of claim 1 further comprising: determining a decay pacing interval.

8. The method of claim 7 further comprising: pacing the cardiac tissue at the decay pacing interval.

9. The method of claim 1 further comprising: determining a minimum atrial pacing interval.

10. The method of claim 9 wherein the first adjusted pacing interval is less than the minimum atrial pacing interval, further comprising: pacing the cardiac tissue at the minimum atrial pacing interval.

11. The method of claim 9 wherein the additional adjusted pacing interval is less than the minimum atrial pacing interval, further comprising: pacing the cardiac tissue at the minimum atrial pacing interval.

12. A method of pacing cardiac tissue using an implantable medical device, comprising:
detecting a first premature atrial contraction, the first premature atrial contraction having a first coupling interval;
calculating a first adjusted pacing interval based on the first coupling interval, wherein the first adjusted pacing interval is shorter than the first coupling interval;
adjusting an initial pacing interval of the cardiac tissue to the first adjusted pacing interval;
detecting a second premature atrial contraction, the second premature atrial contraction having a second coupling interval;
calculating a second adjusted pacing interval based on the second coupling interval, wherein the second adjusted pacing interval is shorter than the second coupling interval; and
further adjusting the first adjusted pacing interval to the second adjusted pacing interval.

13. The method of claim 12 further comprising:
reducing the second adjusted pacing interval to a decay pacing interval.

14. The method of claim 13 further comprising:
determining the decay pacing interval based on the second adjusted pacing interval.

15. The method of claim 12 further comprising:
determining a minimum atrial pacing interval; and
adjusting the initial pacing interval to the minimum atrial pacing interval when the first adjusted pacing interval is less than the minimum atrial pacing interval.

16. The method of claim 12 further comprising:
determining a minimum atrial pacing interval; and
adjusting the first adjusted pacing interval to the minimum atrial pacing interval when the second adjusted pacing interval is less than the minimum atrial pacing interval.

17. The method of claim 12 further comprising: pacing the cardiac tissue at the initial pacing interval.

18. An implantable medical device, comprising: a processor;
at least one pacing circuit operably connected to the processor; and at least one pacing electrode wherein a first premature atrial contraction having a first coupling interval is detected; a first adjusted pacing interval which is shorter than the first coupling interval is calculated based on the first coupling interval; an initial pacing interval is adjusted to the first adjusted pacing interval; a second premature atrial contraction having a second coupling interval is detected; a second adjusted pacing interval which is shorter than the second coupling interval is calculated based on the second coupling interval; and the first adjusted pacing interval is further adjusted to the second adjusted pacing interval.

19. The device of claim 18, further comprising:
a memory location operably connected to the processor for storing the first coupling interval.

20. The device of claim 18, further comprising:
a memory location operably connected to the processor for storing the second coupling interval.

21. The device of claim 18, further comprising:
a memory location operably connected to the processor for storing the first adjusted pacing interval.

22. The device of claim 18, further comprising:
a memory location operably connected to the processor for storing the 15 second adjusted pacing interval.

23. The device of claim 18, further comprising:
a memory location operably connected to the processor for storing a minimum atrial pacing interval.

24. An implantable medical system, comprising:
means for determining a first fibrillation-indicative interval based on a first fibrillation-indicative event;
means for determining a first adjusted pacing interval, wherein the first adjusted pacing interval is shorter than the first fibrillation-indicative interval; means for pacing the cardiac tissue based on the first adjusted pacing interval;
means for determining if the cardiac tissue is captured by pacing at the first adjusted pacing interval;
if the cardiac tissue is not captured, means for determining an additional fibrillation-indicative interval based on an additional earlier fibrillation-indicative event;
means for determining an additional adjusted pacing interval, wherein the additional adjusted pacing interval is shorter than the additional fibrillation indicative interval; and
means for pacing the cardiac tissue based on the additional adjusted pacing interval to reduce atrial fibrillation.

25. The system of claim 24, further comprising:
means for pacing the cardiac tissue based on an initial pacing interval.

26. The system of claim 24, further comprising: means for detecting the first fibrillation-indicative event.

27. The system of claim 24, further comprising:
means for detecting the additional earlier fibrillation-indicative event.

28. The system of claim 24, further comprising: means for determining a decay pacing interval.

29. The system of claim 28, further comprising:
means for pacing the cardiac tissue at the decay pacing interval.

30. The system of claim 24, further comprising: means for determining a minimum atrial pacing interval.

31. The system of claim 30, wherein the first adjusted pacing interval is less than the minimum atrial pacing interval, further comprising: means for pacing the cardiac tissue at the minimum atrial pacing interval.

32. The system of claim 30, wherein the additional adjusted pacing interval is less than the minimum atrial pacing interval, further comprising: means for pacing the cardiac tissue at the minimum atrial pacing interval.

33. An implantable medical system, comprising:
- means for detecting a first premature atrial contraction, the first premature atrial contraction having a first coupling interval;
- means for calculating a first adjusted pacing interval based on the first coupling interval, wherein the first adjusted pacing interval is shorter than the first coupling interval;
- means for adjusting an initial pacing interval of the cardiac tissue to the first adjusted pacing interval;
- means for detecting a second premature atrial contraction, the second premature atrial contraction having a second coupling interval;
- means for calculating a second adjusted pacing interval based on the second coupling interval, wherein the second adjusted pacing interval is shorter than the second coupling interval; and
- means for further adjusting the first adjusted pacing interval to the second adjusted pacing interval.

34. The system of claim 33 further comprising:
- means for reducing the second adjusted pacing interval to a decay pacing interval.

35. The system of claim 34 further comprising:
- means for determining the decay pacing interval based on the second adjusted pacing interval.

36. The system of claim 33 further comprising:
- means for determining a minimum atrial pacing interval; and
- means for adjusting the initial pacing interval to the minimum atrial pacing interval when the first adjusted pacing interval is less than the minimum atrial pacing interval.

37. The system of claim 33 further comprising:
- means for determining a minimum atrial pacing interval; and
- means for adjusting the first adjusted pacing interval to the minimum atrial pacing interval when the second adjusted pacing interval is less than the minimum atrial pacing interval.

38. The system of claim 33 further comprising:
- means for pacing the cardiac tissue at the initial pacing interval.

39. A computer usable medium including a program for pacing cardiac tissue, comprising:
- computer program code that determines a first fibrillation-indicative interval based on a first fibrillation-indicative event;
- computer program code that determines a first adjusted pacing interval, wherein the first adjusted pacing interval is shorter than the first fibrillation-indicative interval;
- computer program code that paves the cardiac tissue based on the first adjusted pacing interval;
- computer program code that determines if the cardiac tissue is captured by pacing at the first adjusted pacing interval;
- if the cardiac tissue is not captured, computer program code that determines an additional fibrillation-indicative interval based on an additional earlier fibrillation-indicative event;
- computer program code that determines an additional adjusted pacing interval, wherein the additional adjusted pacing interval is shorter than the additional fibrillation-indicative interval; and
- computer program code that paces the cardiac tissue based on the additional adjusted pacing interval.

40. The program of claim 39, further comprising:
- computer program code that paces the cardiac tissue based on an initial pacing interval.

41. The program of claim 39, further comprising:
- computer program code that detects the first fibrillation-indicative event.

42. The program of claim 39, further comprising:
- computer program code that detects the additional earlier fibrillationindicative event.

43. The program of claim 39, further comprising: computer program code that determines a decay pacing interval.

44. The program of claim 43, further comprising:
- computer program code that paces the cardiac tissue at the decay pacing interval.

45. The program of claim 39, further comprising:
- computer program code that determines a minimum atrial pacing interval.

46. The program of claim 45, wherein the first adjusted pacing interval is less than the minimum atrial pacing interval, further comprising:
- computer program code that paces the cardiac tissue at the minimum atrial pacing interval.

47. The program of claim 45, wherein the additional adjusted pacing interval is less than the minimum atrial pacing interval, further comprising:
- computer program code that paces the cardiac tissue at the minimum atrial pacing interval.

48. A computer usable medium including a program for pacing cardiac tissue, comprising:
- computer program code that detects a first premature atrial contraction, the first premature atrial contraction having a first coupling interval;
- computer program code that calculates a first adjusted pacing interval based on the first coupling interval, wherein the first adjusted pacing interval is shorter than the first coupling interval;
- computer program code that adjusts an initial pacing interval of the cardiac tissue to the first adjusted pacing interval;
- computer program code that detects a second premature atrial contraction, the second premature atrial contraction having a second coupling interval;
- computer program code that calculates a second adjusted pacing interval based on the second coupling interval, wherein the second adjusted pacing interval is shorter than the second coupling interval; and
- computer program code that further adjusts the first adjusted pacing interval to the second adjusted pacing interval.

49. The program of claim 48 further comprising:
- computer program code that reduces the second adjusted pacing interval to a decay pacing interval.

50. The program of claim 49 further comprising:

computer program code that determines to decay pacing interval based on the second adjusted pacing interval.

51. The program of claim 48 further comprising:

computer program code that determines a minimum atrial pacing interval; and computer program code that adjusts the initial pacing interval to the minimum atrial pacing interval when the first adjusted pacing interval is less than the minimum atrial pacing interval.

52. The program of claim 48 further comprising:

computer program code that determines a minimum atrial pacing interval;

computer program code that adjusts the first adjusted pacing interval to the minimum atrial pacing interval when the second adjusted pacing interval is less than the minimum atrial pacing interval.

53. The program of claim 48 further comprising:

computer program code that paces the cardiac tissue at the initial pacing interval.

* * * * *

UNITED STATES PATENT AND TRADEMARK OFFICE
CERTIFICATE OF CORRECTION

PATENT NO. : 6,650,938 B2  
APPLICATION NO. : 09/842878  
DATED : November 18, 2003  
INVENTOR(S) : Boute Page 1 of 1

It is certified that error appears in the above-identified patent and that said Letters Patent is hereby corrected as shown below:

Col. 19, Line 63, delete "that paves the" and insert --that paces the--.

Signed and Sealed this

Eighteenth Day of July, 2006

JON W. DUDAS  
*Director of the United States Patent and Trademark Office*